(12) United States Patent
Vahey et al.

(10) Patent No.: US 8,072,616 B2
(45) Date of Patent: *Dec. 6, 2011

(54) APPLICATION OF CROSSED TEFLON DIFFUSER TO COATINGS ON ORIENTED SURFACES

(75) Inventors: Paul G. Vahey, Seattle, WA (US);
Gregory J. Werner, Puyallup, WA (US);
Wes W. Quigley, Auburn, WA (US);
Paul H. Shelley, Lakewwod, WA (US)

(73) Assignee: The Boeing Company, Chicago, IL (US)

( * ) Notice: Subject to any disclaimer, the term of this patent is extended or adjusted under 35 U.S.C. 154(b) by 379 days.

This patent is subject to a terminal disclaimer.

(21) Appl. No.: 12/156,484

(22) Filed: Jun. 2, 2008

(65) Prior Publication Data

US 2008/0239284 A1 Oct. 2, 2008

Related U.S. Application Data

(63) Continuation-in-part of application No. 11/566,902, filed on Dec. 5, 2006, now Pat. No. 7,468,519.

(51) Int. Cl.
*G01B 11/28* (2006.01)
(52) U.S. Cl. ........................................ 356/630; 356/445
(58) Field of Classification Search .................... 356/51, 356/625, 630–632; 250/341.2, 458.1; 702/168, 702/170, 172
See application file for complete search history.

(56) References Cited

U.S. PATENT DOCUMENTS

| | | | |
|---|---|---|---|
| 3,693,025 A | | 9/1972 | Brunton |
| 3,792,268 A | * | 2/1974 | Bjerke et al. .................. 250/555 |
| 4,129,781 A | | 12/1978 | Doyle |
| 5,241,366 A | | 8/1993 | Bevis et al. |
| 5,894,127 A | | 4/1999 | Dando et al. |
| 6,078,042 A | | 6/2000 | Fellows |
| 7,223,977 B2 | | 5/2007 | Shelley et al. |
| 2003/0230718 A1 | | 12/2003 | Shelley et al. |
| 2003/0230720 A1 | | 12/2003 | Shelley et al. |
| 2003/0232448 A1 | | 12/2003 | Shelley et al. |
| 2004/0099807 A1 | | 5/2004 | Shelley et al. |
| 2005/0136200 A1 | | 6/2005 | Durell et al. |
| 2005/0226548 A1 | * | 10/2005 | Durkin et al. .................... 385/12 |
| 2005/0263704 A1 | * | 12/2005 | Shelley et al. ........... 250/339.01 |
| 2006/0056021 A1 | * | 3/2006 | Yeo et al. ...................... 359/460 |
| 2007/0038041 A1 | | 2/2007 | Yang et al. |

FOREIGN PATENT DOCUMENTS

DE 10 2005 025848 2/2007
WO WO 2005/077135 8/2005

* cited by examiner

*Primary Examiner* — Tarifur Chowdhury
*Assistant Examiner* — Tara S Pajoohi
(74) *Attorney, Agent, or Firm* — Armstrong Teasdale LLP

(57) ABSTRACT

A system and method for measuring coating thickness upon a substrate containing directionally oriented elements is disclosed. A near infrared light is directed upon the coating and reflected near infrared light is collected to determine the coating thickness. A pair of stacked and crossed diffuser elements is placed between the light source and the sample, and between the sample and the reflected near infrared light collector to improve the accuracy of the measurement, especially for coating thickness of less than about 2 mils and for coatings on substrates containing directionally oriented components. Each diffuser element is formed of a polytetrafluoroethylene fluoropolymer (PTFE) film.

16 Claims, 2 Drawing Sheets

APPLICATION OF CROSSED TEFLON DIFFUSER TO COATINGS ON ORIENTED SURFACES

CROSS-REFERENCE TO RELATED APPLICATIONS

This patent application is a continuation-in-part of, commonly-owned U.S. patent application Ser. No. 11/566,902, filed Dec. 5, 2006, now U.S. Pat. No. 7,468,519 and entitled "Near Infrared Light Diffuser", which application is incorporated herein by reference.

FIELD OF THE DISCLOSURE

The present disclosure is directed to a method and apparatus for measuring a coating thickness on substrates containing directionally oriented components, including fiber-reinforced polymer composites, using a Near Infra Red (NIR) absorbance technique and a diffuser assembly including two crossed diffuser elements. The method and apparatus minimizes the changes in signal due to directionally oriented components contained within a substrate during measurements where the orientation of the substrate is unknown compared to the measurement apparatus.

BACKGROUND OF THE DISCLOSURE

Surfaces of many different materials are coated in a variety of applications for a wide range of motives, from aesthetic reasons to protection of the surface of the underlying substrate against physical and environmental damage. Often it is desirable to determine the thickness of these coatings, especially for applications where extremely thin coatings are critical on polymer or composite substrates containing directionally oriented inclusions, such as fiber-reinforced polymer composites.

Such directional orientation can cause undesirable variations in spectroscopic measurements, which ultimately can negatively impact measurements of thin coatings carried thereon.

In attempting to measure thicknesses of coatings, it has been found that small differences in orientation of the sensor with respect to the substrate can result in deleterious variations in spectral data. Thus, there is a need to eliminate the variation in spectral data due to differences in orientation of the sensor relative to the substrate and thus yield reproducible coating measurements that are independent of the sensor with respect to the substrate.

Most known nondestructive coating measurement techniques are limited in their applicability for polymer composite and other non-metal substrates. In one known method, ultrasound testing is used to determine thickness of coatings on surfaces of composite or plastic substrates. However, ultrasound testing has been shown to have subjective data interpretation issues and therefore can be inconsistent and unreliable. Moreover, ultrasound techniques have great difficulty in determining coating thicknesses below approximately 0.002 inches (2 mils). In another known method, the same sensor and substrate alignment is maintained for all measurements. This is difficult to achieve, especially in cases where the coating is opaque. With this method, reproducibility is difficult because small variations in orientation negatively impact reproducibility of spectroscopic data. Many of the known nondestructive methods do not correct for orientation effects. Current methods to compensate for orientation effects are based on anecdotal information and include making measurements at several orientations and using the average result.

Near infrared (NIR) spectroscopy has been successfully used to measure coating thicknesses on a variety of substrate materials. However, to date, there has been significant difficulty in using NIR methods for high specular reflectance coatings, coatings of less than 2 mils, and coatings on oriented substrates. One problem encountered in obtaining accurate and reproducible thickness measurements is specular reflectance from the coating that interferes with the NIR diffuse reflectance measurements. The disclosure of the co-pending, commonly-owned application having U.S. Ser. No. 11/566,902, filed Dec. 5, 2006 proposes the use of a diffuser element between the light source and the substrate on which the coating thickness is being measured. The diffuser described in the above-mentioned disclosure somewhat reduced variation due to orientation differences, but did not eliminate them.

However, in attempting to measure opaque coatings (for example, paint, sealants, protective films, etc.) on substrates containing directionally oriented components, including fiber-reinforced polymer composites, the substrate orientation is not observable.

Therefore, there is an unmet need to provide an apparatus and method to accurately and nondestructively measure the thickness of thin coatings applied to substrates containing directional oriented components, such as fiber-reinforced polymer composites, without regard for relative orientation of the sensor or the substrate.

SUMMARY OF THE DISCLOSURE

The disclosure provides for apparatus and method for measuring thicknesses of coatings on substrates containing directionally oriented elements while minimizing the effects of optically scattered light reflected from such elements. The apparatus includes a diffuser assembly of stacked and crossed diffuser elements. The method involves transmitting NIR radiation through the stacked and crossed diffuser elements of the diffuser assembly towards a sample, and collecting the reflected NIR light after it passes again through the diffuser assembly.

Systems and methods to measure coating thicknesses on substrate surfaces using NIR measurement processes have been developed, as disclosed in the currently pending, co-owned, published application bearing U.S. Patent Publication Number 2005/0263704, filed May 16, 2005, and co-owned U.S. Pat. No. 6,903,339, filed Nov. 26, 2002, both of which are incorporated herein by reference. These systems, however, are limited in their ability to accurately measure coating thicknesses below 2 mils, to accurately measure coating thicknesses when the coating has a shiny finish, and to accurately measure coating thicknesses on substrates containing directionally oriented elements, such as reinforcing fibers.

By placing a diffuser assembly of the type disclosed in detail herein between the surface bearing the coating, on the one hand, and a NIR probe including a NIR light source and a reflected NIR light collector, on the other hand, an improvement has been made in accurately measuring coating thickness in all of these situations.

The disclosure provides a method of determining coating thickness using a NIR probe and a diffuser assembly including two layers of PTFE thin film manufactured to Military Specification MIL-T-27730A. The diffuser assembly can be secured within the probe or attached to the exterior of the probe.

The diffuser assembly of the present disclosure is formed of two layers of a polytetrafluoroethylene (PTFE) fluoropolymer thin film, such as Teflon® made by E.I. du Pont de Numours and Company, manufactured to Military Specification MIL-T-27730A. The film may be of low density. The PTFE film does not have observable NIR absorbance bands but scatters NIR light. The two layers of PTFE film are arranged normal to, and atop, one another. The diffuser assembly is arranged between the measuring device and the coating to be measured via reflectance. Thus the light leaves the source, passes through the diffuser assembly, interacts with the coating and substrate, and passes through the diffuser assembly again before reaching the detector assembly. This arrangement not only minimizes the specular reflectance due to a single light source, but also makes the light source diffuse in nature, thereby eliminating specular reflectance entirely.

The NIR probe includes a NIR light source and a light collector assembly, and an NIR sensitive detection system. The NIR sensitive detection system may be built into a handheld unit. Calibration of the NIR probe, if required, is performed as disclosed in the prior co-owned application U.S. Ser. No. 11/566,902.

The diffuser assembly of the disclosure minimizes specular reflectance effects in light scattering materials, and enables accurate and reproducible thickness measurements, especially of coatings of less than 2 mils in thickness and/or with shiny surfaces. This is accomplished by improving the measurement of the diffuse reflected NIR light and minimizing specular reflectance from substrate irregularities and coating surface reflections, which could negatively impact the thickness measurement. Specular reflectance, especially from substrate irregularities in composite and oriented substrates, is more problematic in NIR thickness measurements for coatings that are less than 2 mils.

The diffuser assembly of the disclosure may be used to measure the thickness of a paint, primer, or other coating on a composite or oriented substrate. The coating may be transparent or opaque. The coating may be a polyurethane-base paint. It is further understood that measurement of other coatings, such as other paint materials and primers, including epoxy primers, latex paint, enamel paint, filled stains and varnishes, and other like coatings, may be made. The coating may be formed of two or more layers of different coating materials.

Further aspects of the method and system are disclosed herein. The features as discussed above, as well as other features and advantages of the present disclosure will be appreciated and understood by those skilled in the art from the following detailed description and drawings.

DETAILED DESCRIPTION OF THE DISCLOSURE

The present disclosure now will be described more fully hereinafter with reference to the accompanying drawing, in which a preferred embodiment is shown. This disclosure may, however, be embodied in many different forms and should not be construed as limited to the embodiments set forth herein; rather, these embodiments are provided so that this disclosure will be thorough and complete and will fully convey the scope of the disclosure to those skilled in the art.

Figure 1:
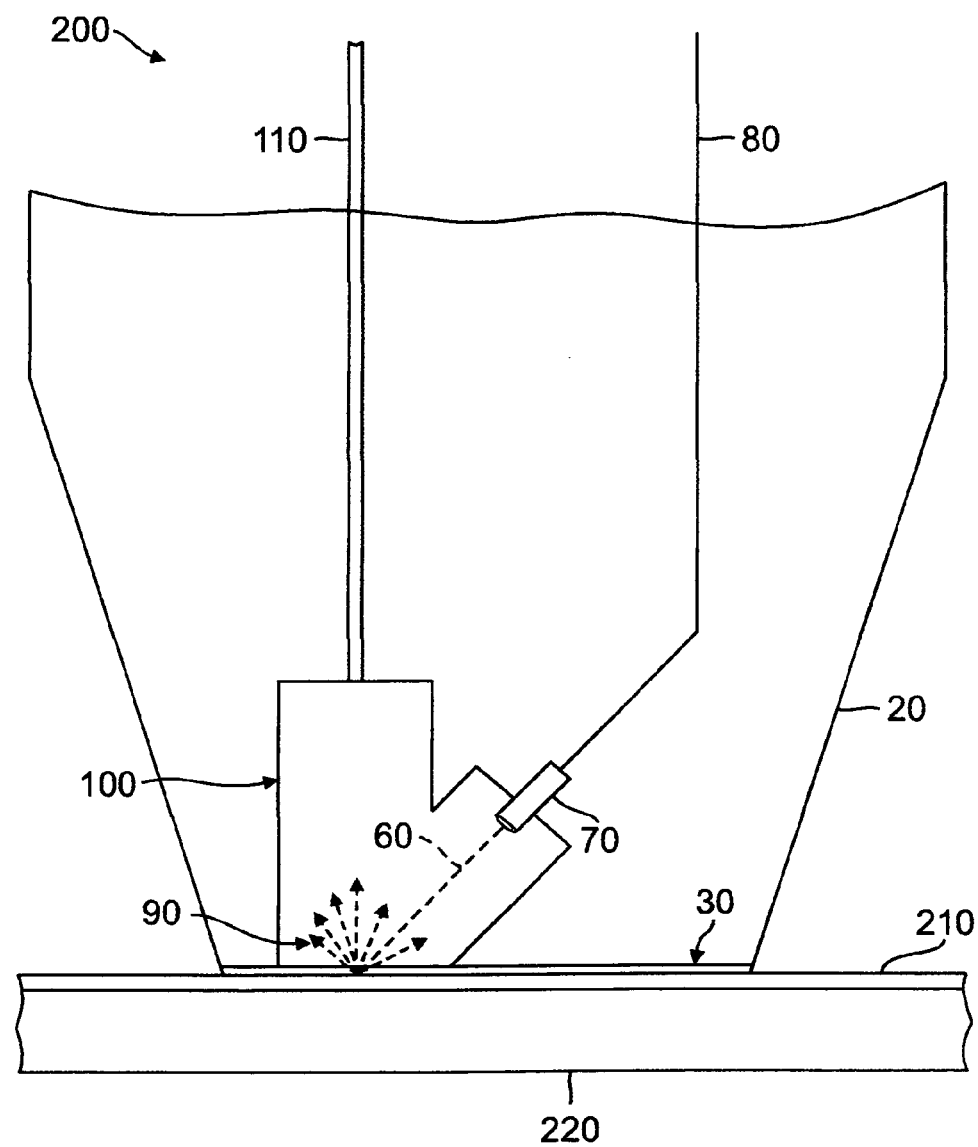
FIG. 1 shows an embodiment of the NIR thickness measurement system of the present disclosure during coating measurement.

Referring to FIG. 1, the NIR thickness measurement system 200 in accordance with a preferred embodiment of the present disclosure includes a NIR diffuse reflection probe 20, hereinafter referred to as a probe 20, and a diffuser assembly 30. The diffuser assembly 30 may be incorporated into, or attached to the nose of, the probe 20 as discussed below. Alternatively, the diffuser assembly 30 may be provided as a separate element and used with the probe 20 by physically disposing the assembly 30 between the nose of the probe 20 and the coating 210 carried by the substrate 220. Calibration of the NIR probe, if required, is performed as disclosed in the prior co-owned application U.S. Ser. No. 11/566,902, except the diffuser assembly 30 of the present disclosure is used instead of the diffuser apparatus disclosed in the prior application.

The NIR probe 20 includes a NIR light beam source 70 powered by a light source power supply 80, a NIR light collector 100 with a fiber optic light pickup 110. When making use of the probe 20, the diffuser assembly 30 is placed between the coating 210 and the probe 20, such that the diffuser assembly and the coating 210 are in direct sequential contact. The NIR light beam source 70 directs a light beam 60 first through the two PTFE layers of the diffuser assembly 30 and then on the coating 210 carried by the substrate 220. The NIR light source 70 receives power from a light source power supply 80. The reflected NIR light 90 passes again through the two layers of the diffuser assembly 30 and is then collected by the NIR light collector 100 and fed via the fiber optic light pick-up 110 to a spectrometer (not shown) for measurement. An absorbance spectrum is calculated as −log(thickness spectrum/reference spectrum).

The method and apparatus of the present disclosure will minimize changes in signal strength due to directionally oriented components contained within a substrate during measurements, especially where the orientation of the substrate is unknown compared to the measurement apparatus.

Figure 2:
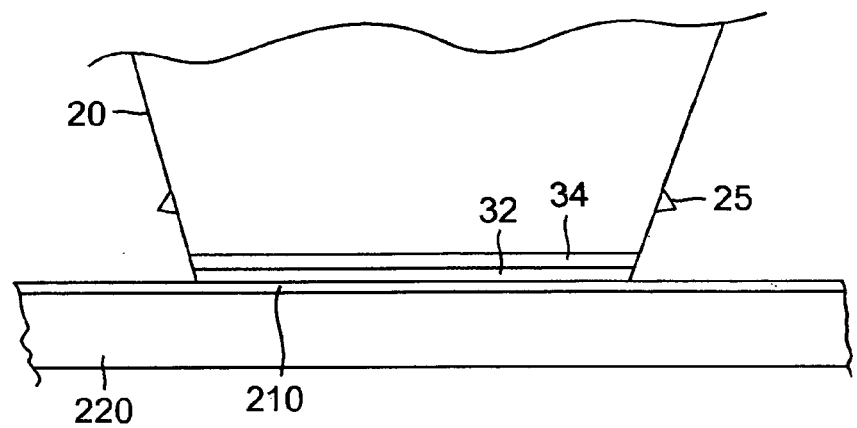
FIG. 2 is a close up view of the NIR probe and the diffuser assembly of the present disclosure.
Figure 3:
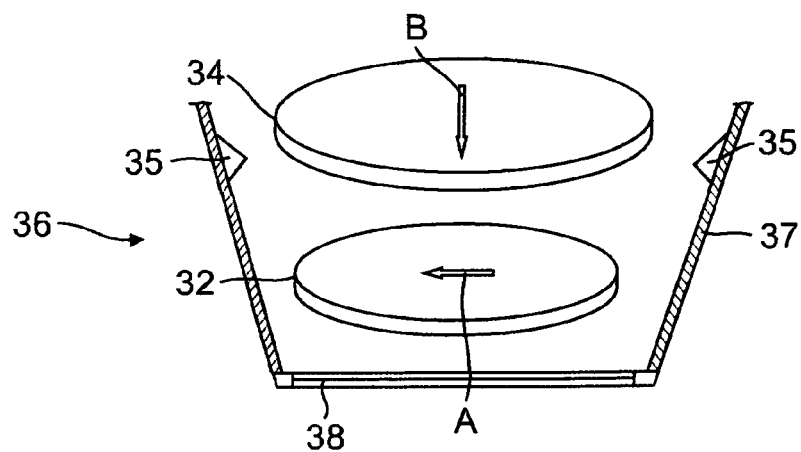
FIG. 3 shows the two diffuser layers arranged relative to each other and adapted to be mounted to the nose of the NIR probe.

The diffuser assembly 30 is shown in greater detail in FIGS. 2 and 3, and is seen to include two layers 32, 34 of low density Teflon® thin film. Each layer will have a thickness of about 3 mils to about 4 mils. Commercially available Teflon® plumbers tape, or a custom Teflon® sheet, meeting Military Specification MIL-T-27730A may be used for each of the two layers of the diffuser assembly. FIG. 3 shows the two layers 32, 34 of PTFE film used in the diffuser of the present disclosure. The two layers 32, 34 can be placed directly at the nose of the probe 20 (as shown in FIG. 2), or they can be used with a support 36 (FIG. 3). The layers will have similar shapes, but they can be of any shape, including one that corresponds to the shape of the nose of probe 20. When used with the support 36, the layer 32 is placed atop the centrally disposed, transparent, window 38, the circumference of which could be as great as the diameter of the layer 32, and the second layer 34 is then disposed directly atop layer 32. The support 36 may be provided with an upstanding circumferential wall 37 which can act to contain and insure registration of the two layers 32, 34 one atop the other when mounted in the support 36. In addition, the upstanding wall can be provided with a securement element, such as a detent 35 corresponding to an optional detent 25 carried by the outer nose wall of the probe 20. The detents 25 and 35 would be complementarily configured so as to insure secure engagement of the support 36 with the nose of the probe 20. The machine direction A, B of the two layers 32, 34 are crossed, and therefore perpendicular, relative to one another.

The diffuser assembly 30 is disposed at the nose of the probe 20. In one embodiment, the diffuser assembly can be unitary with the nose of the probe. In another embodiment, the diffuser assembly can be a separate component that is attachable to the nose of the probe. In either case, the diffuser assembly is arranged relative to the probe in such a manner as to diffuse reflected NIR light reaching a NIR light collector 100 of the probe 20 after it passes through the diffuser assembly 30.

The diffuser of the disclosure minimizes specular reflectance effects in light scattering materials, and enables accurate and reproducible thickness measurements, especially of coatings of less than 2 mils thickness and/or with shiny surfaces. This is accomplished by improving the measurement of the diffuse reflected NIR light and minimizing specular reflectance from substrate irregularities and coating surface reflections, which otherwise can negatively impact the thickness measurement. Specular reflectance, especially from substrate irregularities in composite and oriented substrates, is much more problematic in NIR thickness measurements for coatings that are less than 2 mils.

The coating thickness measurement method of the disclosure may be used to measure the thickness of a paint, primer, or coating upon a composite or oriented substrate. The coating may be opaque or transparent. The coating may be a polyurethane-base paint. It is understood, however, that measurement of other coatings, such as other paints materials and primers, including epoxy primers, latex paint, enamel paint, filled stains and varnishes, and other like coatings, may also be made.

The coating may be formed of two or more layers of different coating materials. The NIR measurement method may be used to determine the overall coating thickness when the outer coating layer is opaque and less than about 12 mils thick. Also, the NIR measurement method may be used to determine the overall coating thickness when the outer coating is transparent and less than about 40 mils. The diffuser assembly may be used in measuring layered coatings, and has shown good results in reducing specular reflectance, especially when the outer coating is shiny.

The substrate may be formed of metal, plastic, wood, fiberglass, or a composite woven material, and in the latter case may be reinforced with fiber reinforcing structural elements dispersed within the resin matrix.

The coating that can be measured with the present system may be a primer, paint, or other coating applied to a substrate. The coating may be opaque or transparent. The coating may be a polyurethane based paint. It is understood, however, that measurement of other coatings, such as vapor barriers, sacrificial materials and primers, including epoxy primers, latex paint, enamel paint, filled stains and varnishes, and other like coatings, may also be made. The coating may be formed of layers of different coating materials. The NIR measurement technique will determine the overall thickness of the coating.

The coating measurement system of the present disclosure is not limited to flat geometry of a coated surface; the principles and teachings as set forth herein will also support measurements of thicknesses of coatings upon a variety of substrate geometries.

While there has been described a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment described as the best mode contemplated for carrying out this disclosure, but that the disclosure will include all embodiments falling within the scope of the appended claims.

The invention claimed is:

1. A system for measuring the thickness of a coating on a substrate containing directionally oriented components, comprising:
   an NIR probe including an NIR light collector; and
   a diffuser assembly consisting essentially of two stacked and crossed diffuser elements, wherein the diffuser elements are positioned between the NIR light collector and the coating on the substrate such that light initially passes through the diffuser elements before striking the coating on the substrate and subsequently passes through the diffuser elements after being reflected from the coating on the substrate.

2. The system of claim 1, wherein each of said diffuser elements is manufactured to military specification MIL-T-27730A.

3. The system of claim 1, and further including an NIR light source.

4. The system of claim 1, and further wherein the two diffuser elements each comprise polytetrafluoroethylene fluoropolymer thin film.

5. The system of claim 4, further comprising wherein the polytetrafluoroethylene fluoropolymer thin film is between about 3 mils and about 4 mils thick.

6. A method for measuring a coating thickness, comprising:
   providing a calibrated NIR probe comprising a NIR light collector;
   arranging a diffuser assembly between the NIR probe and the coating, the diffuser assembly consisting essentially of two tape diffuser elements disposed one atop another, and normal to one another, wherein the diffuser elements are positioned between the NIR light collector and the coating such that light initially passes through the diffuser elements before striking the coating and subsequently passes through the diffuser elements after being reflected from the coating; and
   assessing light values reflected from the coating and collected by the NIR light collector, wherein the thickness of the coating can be determined.

7. The method of claim 6, further comprising providing each of the diffuser elements as polytetrafluoroethylene fluoropolymer thin film.

8. The method of claim 6, further comprising providing each of the diffuser elements as PTFE film manufactured to Military Specification MIL-T-27730A.

9. An NIR light diffuser assembly, consisting essentially of:
   two thin film diffuser elements arranged one atop the other and one normal to the other, at least a portion of said diffuser elements being disposed directly in contact with one another such that light initially passes through said diffuser elements before striking a coating and subsequently passes through said diffuser elements after being reflected from the coating, each said diffuser element comprising a segment of PTFE thin film.

10. The assembly of claim 9, wherein each of said diffuser elements is manufactured to military specification MIL-T-27730A.

11. The NIR diffuser assembly of claim 9, and further including a housing for maintaining the two diffuser elements in position relative to one another.

12. The NIR diffuser assembly of claim 11, wherein a portion of the housing includes detent elements for securely engaging an NIR probe.

13. A method for determining a coating thickness on a substrate having directionally oriented components, comprising:
  providing a NIR probe having a nose, an NIR light source for directing NIR light through the nose, and an NIR light collector;
  arranging the coating on the substrate in close proximity to the NIR probe nose;
  positioning a diffuser assembly consisting essentially of a pair of diffuser elements, arranged atop, adjacent, and normal to one another, between the coating and the NIR probe nose such that light from the NIR light source initially passes through the pair of diffuser elements before striking the coating and subsequently passes through the pair of diffuser elements after being reflected from the coating;
  directing NIR light from the NIR light source at the coating;
  collecting reflected NIR light reflected from the coating using the NIR light collector; and
  determining the coating thickness from analysis of the collected reflected NIR light.

14. The method of claim 13, and further comprising the step of providing a housing for the two diffuser elements.

15. The method of claim 13, wherein each of the diffuser elements comprise a layer of PTFE film manufactured according to Military Specification MIL-T-27730A.

16. The method of claim 13, and further comprising the step of securing the diffuser elements to the NIR probe.

* * * * *